United States Patent [19]

Goldstein et al.

[11] 4,258,152
[45] Mar. 24, 1981

[54] PENTAPEPTIDE MODIFIED RESIN

[75] Inventors: Gideon Goldstein, Short Hills, N.J.; David H. Schlesinger, Lombard, Ill.

[73] Assignee: Sloan-Kettering Institute for Cancer Research, New York, N.Y.

[21] Appl. No.: 47,909

[22] Filed: Jun. 12, 1979

Related U.S. Application Data

[60] Division of Ser. No. 6,893, Jan. 26, 1979, Pat. No. 4,190,646, which is a continuation-in-part of Ser. No. 851,777, Nov. 15, 1977, abandoned, which is a continuation-in-part of Ser. No. 631,175, Nov. 11, 1975, abandoned.

[51] Int. Cl.³ .................................................. C08F 8/30
[52] U.S. Cl. .......................................... 525/327; 260/9; 525/58; 525/61; 525/332; 525/335; 525/386; 525/381; 525/382; 525/379; 525/380; 528/310; 528/328; 536/30
[58] Field of Search ................... 528/328, 310; 260/9, 260/58; 525/61, 327, 332, 335, 380, 386, 382, 381, 379; 536/30, 11.79

[56] References Cited

U.S. PATENT DOCUMENTS 3,888,837  6/1975  Tsumita et al. ............... 260/112.5 R
3,943,119  3/1976  Tsumita et al. ............... 260/112.5 R
4,002,740  1/1977  Goldstein ...................... 260/112.5 R
4,077,949  3/1978  Goldstein ...................... 260/112.5 R

OTHER PUBLICATIONS

Stewart et al.—Solid Phase Peptide Synthesis, 1969, pp. 1–5.
Concise Chemical and Technical Dictionary, Third Edition, 1974, p. 40.

Primary Examiner—Harold D. Anderson
Attorney, Agent, or Firm—Lowe, King, Price & Becker

[57] ABSTRACT

There are disclosed polypeptide compositions having the following amino acid sequence as the active site:

ARG-LYS-ASP-VAL-TYR

These polypeptides have the capability of inducing the differentiation of T-lymphocytes but not of complement receptor (CR+) B-lymphocytes and thus are useful in a number of therapeutic areas. Also provided are derivatives of the pentapeptide, novel intermediate polypeptides, methods of manufacture of the peptides, therapeutic compositions, and methods for use of the compositions.

2 Claims, No Drawings

PENTAPEPTIDE MODIFIED RESIN

The invention described herein was made in the course of work conducted under a grant or award from the U.S. Department of Health, Education and Welfare.

CROSS-REFERENCE TO RELATED APPLICATIONS

This application is a division of parent application Ser. No. 6,893 filed Jan. 26, 1979, now U.S. Pat. No. 4,190,646, dated Feb. 26, 1980, which is a continuation-in-part of Ser. No. 851,777 filed Nov. 15, 1977, now abandoned, which is a continuation-in-part of Ser. No. 631,175 filed Nov. 11, 1975, and now abandoned.

BACKGROUND OF THE INVENTION

1. Field of the Invention

This invention relates generally to new polypeptides, to methods for preparation of the new polypeptides, and fields of use for the polypeptides.

2. Description of the Prior Art

It is well known that many polypeptides have been isolated from various organs of animals. Until about the past decade, however, very little was known about the thymus, an organ which in man comprises about 0.8% of his body weight at birth, although it has been previously hypothesized that a neuromuscular blocking substance existed in the thymus and that thymic hormone affected the development of the immune system. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus is known to be a compound organ consisting of an epithelial stroma derived from the third branchial arch and lymphocytes derived from stem cells originating in haemopoietic tissues, Goldstein et al, *The Human Thymus*, Heinemann, London, 1969. Lymphocytes are differentiated within the thymus and leave as mature thymus-derived cells, called T cells, which circulate to the blood, lymph, spleen, and lymph nodes. The induction of stem cell differentiation within the thymus appears to be mediated by secretions of the epithelial cells of the thymus but difficulties with bioassays had previously hindered the complete isolation and structural characterization of any hormones which may be present.

To provide an understanding of the importance of the differentiating biological characteristics of the polypeptides of this invention, it should be noted that the function of the thymus in relation to immunity may be broadly stated as the production of thymus-derived cells, or lymphocytes, which are called T cells. T cells form a large proportion of the pool of recirculating small lymphocytes. T cells have immunological specificity and are directly involved in cell-mediated immune responses (such as homograft responses), as effector cells. T cells, however, do not secrete humoral antibodies as these antibodies are secreted by cells derived directly from the bone marrow independently of the thymic influence and these latter cells are termed B cells. However, for many antigens, B cells require the presence of appropriately reactive T cells before they can produce antibodies. The mechanism of this process of cell cooperation is not yet completely understood.

From this explanation, it may be said that in operational terms, the thymus is necessary for the development of cellular immunity and many humoral antibody responses and it affects these systems by inducing, within the thymus, the differentiation of haemopoietic stem cells to T cells. This inductive influence is mediated by secretions of the epithelial cells of the thymus, that is, the thymic hormones.

Further, to understand the operation of the thymus and the cell system of lymphocytes, and the circulation of lymphocytes in the body, it should be pointed out that stem cells arise in the bone marrow and reach the thymus by the blood stream. Within the thymus, stem cells become differentiated to immunologically competent T cells, which migrate to the blood stream and together with B cells, circulate between the tissues, lymphatics, and the blood stream.

The cells of the body which secrete antibody also develop from haemopoietic stem cells but their differentiation is not determined by the thymus. Hence, they are termed bone marrow-derived cells or B cells. In birds they are differentiated in an organ analogous to the thymus, which is called the Bursa of Fabricius. In mammals no equivalent organ has been discovered and it is thought that B cells differentiate within the bone marrow. The physiological substances dictating this differentiation remain completely unknown.

It has been known for some time that the thymus is connected with the immunity characteristics of the body and therefore great interest has been indicated in substances which have been isolated from the thymus. In this regard, there have been published in recent years a relatively large body of articles based on scientific work relating to materials which are present in bovine thymus. In fact, the Applicants have published a number of articles which relate to research in this area. Pertinent publications may be found, for example, in *The Lancet*, July 20, 1968, pp. 119–122; *Triangle*, Vol. 11, No. 1, pp. 7–14, 1972; *Annals of the New York Academy of Sciences*, Vol. 183, pp. 230–240. 1971; *Clinical and Experimental Immunology*, Vol. 4, No. 2, pp. 181–189, 1967; *Nature*, Vol. 247, pp. 11–14, 1974; *Proceedings of the National Academy of Sciences, U.S.A.*, Vol. 71, pp. 1474–1478, 1974; *Cell*, Vo. 5, pp. 361–365, and pp. 367–370, 1975; and *Lancet*, Vol. 2, pp. 256–259, 1975.

In the article by Goldstein and Manganaro in *Annals of the New York Academy of Sciences*, Vol. 183, pp. 230–240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin," was believed to cause myositis but it was further indicated that this polypeptide had not been isolated although it appeared to be a polypeptide of approximately 7,000 molecular weight, had a strong net positive charge and was retained on CM-Sephadex at a pH of 8.0.

In the publication "Nature," 247, 11, Jan. 4, 1975, there are described products identified as Thymin I and Thymin II which were found to be new polypeptides isolated from bovine thymus which have particular uses in various therapeutic areas. Because of the use of similar names for other products isolated from the thymus in the prior art, these Thymin I and Thymin II products are now named as Thymopoietin I and Thymopoietin II. These products and processes are described in U.S. Pat. No. 4,077,949, issued Mar. 7, 1978, from Ser. No. 606,843, filed Aug. 22, 1975, which is a continuation-in-part of application Ser. No. 429,202, filed Dec. 28, 1973, and now abandoned.

In issued U.S. Pat. No. 4,002,602, dated Jan. 11, 1977, which is a continuation-in-part of application Ser. No. 449,686, filed Mar. 11, 1974, now abandoned, there are disclosed long chain polypeptides described as Ubiquitous Immunopoietic Polypeptides (UBIP), which polypeptide is a 74-amino acid polypeptide characterized by its ability to induce in vitro, in nanogram concentrations, the differentiation of both T-cell and B-cell immunocytes from precursors present in bone marrow or spleen. Thus the polypeptide is useful in therapeutic areas involving thymic or immunity deficiencies and the like.

In issued U.S. Pat. No. 4,002,740, issued Jan. 11, 1977 there are disclosed synthesized tridecapeptide compositions which have the capability of inducing the differentiation of T-lymphocytes but not of complement receptor β-lymphocytes. This polypeptide thus exhibited many of the characteristics of the long chain polypeptides isolated and named as thymopoietin in above-mentioned U.S. Pat. No. 4,077,949.

The present invention provides a synthesized five-amino acid polypeptide having a definite active site sequence which has been found to exhibit many of the characteristics of the long chain polypeptide isolated and name as Thymopoietin in the above publications and U.S. Pat. No. 4,077,949 and the tridecapeptide described in U.S. Pat. No. 4,002,740.

SUMMARY OF THE INVENTION

It is accordingly one object of this invention to provide new polypeptides which are important biologically.

A further object of the invention is to provide new polypeptides which have the ability in nanogram concentrations to induce differentiation of bone marrow cells to T cells thus giving rise to thymus-derived lymphocytes and thereby are highly useful in the immunity system of humans and animals.

A further object of the invention is to provide novel intermediate products, methods for synthesizing the novel polypeptides of this invention, as well as compositions and methods for use in biological actions.

Other objects and advantages of the invention will become apparent as the description thereof proceeds.

In satisfaction of the foregoing objects and advantages there is provided by this invention novel polypeptides having the following sequence as the active site:

-ARG-LYS-ASP-VAL-TYR-

There are also provided novel peptide-resin intermediates formed in the preparation of the polypeptides of this invention, which intermediates have the following sequence:

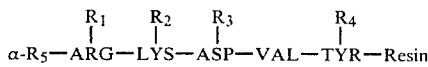

as well as the peptide intermediates freed from the resin and other protecting groups, wherein $R_1$, $R_2$, $R_3$, $R_4$ and $R_5$ represent protecting groups on the amino acids indicated if such groups are necessary, and the resin is a solid phase polymer which acts as a support for the reaction. Also provided are procedures for preparation of the polypeptides of the invention by solid phase peptide synthesis, as well as therapeutic compositions containing the polypeptides, and methods for administration of the polypeptides to humans and animals for effecting biological actions thereon.

DESCRIPTION OF PREFERRED EMBODIMENTS

As indicated above, this invention is concerned with new polypeptides having therapeutic value in various areas, intermediates formed in the preparation of the polypeptides, therapeutic compositions, and methods for their use utilizing the polypeptides of this invention, and methods for manufacture of the polypeptides.

In the main embodiment of the present invention, there are provided polypeptides which have the following amino acid sequence as the active site:

ARG-LYS-ASP-VAL-TYR (I)

In a further embodiment, there are provided pentapeptides containing the above mentioned sequence as the active site and which may be described by the following general formula:

R-NH-ARG-LYS-ASP-VAL-TYR-COR' (II)

wherein R and R' are substituents on the pentapeptide sequence which do not substantially affect the biological activity of the basic active sequence. By this statement is meant that the terminal amino acids on this pentapeptide chain may be modified without departing from the scope of the invention when functional groups or derivatives (R and R') are placed on these terminal amino acids which do not substantially affect the biological activity of the molecule. Thus it is to be understood that the terminal amino and carboxylic acid groups are not essential to the biological activity of the pentapeptide as in some polypeptides. Therefore, it is considered that the scope of the present invention is inclusive of these pentapeptides which are terminally unsubstituted and which are terminally substituted by one or more functional groups which do not substantially affect the biological activity disclosed herein.

From this statement it will be understood that these functional groups include such normal substitution as acylation on the free amino group and amidation on the free carboxylic acid group, as well as the substitution of additional amino acids and polypeptides. In these aspects the pentapeptides of this invention appear to be unique since the pentapeptides exhibit the same biological activity as long chain natural peptides in which this pentapeptide sequence forms a portion or occurs therein. It is believed therefore that the activity requirements of the molecule are generated by stereochemistry of the molecule, that is, the particular "folding" of the molecule. In this regard, it should be understood that polypeptide bonds are not rigid but flexible, and may exist as sheets, helices, and the like. As a result, the entire molecule is flexible and will "fold" in a certain way. In the present invention it has been discovered that the pentapeptide "folds" in the same manner as the long chain natural polypeptide and therefore exhibits the same biological characteristics. For this reason, the pentapeptide may be substituted by various functional groups so long as the substituents do not substantially affect the biological activity or interfere with the natural "folds" of the molecule.

The ability of the molecule to retain its biological activity and natural folding is clearly illustrated by the fact that the pentapeptide sequence of this invention exhibits the same biological characteristics as the natural forty-nine amino acid disclosed as Thymopoietin in U.S. Pat. No. 4,077,949 and in the publication, Nature, 247, 11, 1975. Moreover, the pentapeptide fragment or sequence exhibits the same biological characteristics as the synthesized tridecapeptide disclosed in Cell, Vol. 5, 367–370, August, 1975, and in U.S. Pat. No. 4,002,740. In both of these long chain polypeptides, the pentapeptide of this invention may be identified within the molecule but only in combination with the other amino acids described therein. However, these publications are direct evidence that the pentapeptide of this invention is the active site since the biological activities are the same and the amino acids and peptide chains substituted on the terminal amino acids do not affect the biological characteristics of the basic pentapeptide fragment.

In view of this discussion therefore, it will be understood that R and R' in formula II can be any substituent that does not substantially affect the biological activity of the basic active sequence. Thus, for purposes of illustration R and R' may be any of the following substituents:

| R | R' |
|---|---|
| Hydrogen | OH |
| $C_1$–$C_7$ alkyl | $NH_2$ |
| $C_5$–$C_{12}$ aryl | $NHR_7$ |
| $C_6$–$C_{20}$ alkaryl | $N(R_7)_2$ |
| $C_6$–$C_{20}$ aralkyl | $OR_7$ |
| $C_1$–$C_7$ alkanoyl | |
| $C_2$–$C_7$ alkenyl | |
| $C_2$–$C_7$ alkynyl | | wherein $R_7$ is $C_1$–$C_7$ alkyl, $C_2$–$C_7$ alkenyl, $C_2$–$C_7$ alkynyl, $C_6$–$C_{20}$ aryl, $C_6$–$C_{20}$ alkaryl, or $C_6$–$C_{20}$ aralkyl.

As pointed out above however, R and R' can also be amino acid groups or residues of polypeptide chains having 1 to 20 carbon atoms. The following are illustrative:

| R | R' |
|---|---|
| GLN | VAL |
| GLU | GLN |
| GLY | LEU |
| GLU—GLN | TYR |
| GLY—GLN | VAL—GLN |
| GLY—GLU | VAL—LEU |
| GLY—GLU—GLN | VAL—TYR |
| | GLN—LEU |
| | GLN—TYR |
| | GLN—VAL |
| | LEU—TYR |
| | LEU—LEU |
| | TYR—LEU |
| | VAL—GLN—LEU |
| | VAL—GLN—LEU—TYR |

In a more specific embodiment of the invention, there is provided a novel pentapeptide having the following sequence:

R-HN-ARG-LYS-ASP-VAL-TYR-COR'      (III)

wherein R is hydrogen, $C_1$–$C_7$ alkyl, e.g. methyl, ethyl, $C_5$–$C_{12}$ aryl, e.g. phenyl, or $C_1$ to $C_7$ alkanoyl, e.g. acetyl or propionyl and R' is OH, $NH_2$, $NHR_7$, or $N(R_7)_2$. The most preferred polypeptides are those wherein R is hydrogen and R' is OH.

Also included within the scope of the invention are the pharmaceutically acceptable salts of the pentapeptides.

As acids which are able to form salts with the pentapeptide, there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid or sulfanylic acid, for instance.

In the above structures the amino acid components of the peptides are identified by abbreviations for convenience. These abbreviations are as follows:

| Amino Acid | Abbreviated Designation |
|---|---|
| Glycine | GLY |
| L-glutamic acid | GLU |
| L-glutamine | GLN |
| L-arginine | ARG |
| L-lysine | LYS |
| L-aspartic acid | ASP |
| L-valine | VAL |
| L-tyrosine | TYR |
| L-leucine | LEU |

The polypeptide sequence active site of this invention is a five amino acid peptide which has been found to exhibit characteristics similar to the 49-amino acid polypeptide isolated from bovine thymus as disclosed in U.S. Pat. No. 4,077,949. The peptides of this invention are particularly characterized in their ability to induce the selective differentiation of Thy-1+ T cells (but not CR+ B cells), in concentrations of 1 ng to 10 $\mu$g/ml. Thy-1 is a differentiation alloantigen present on T cells but not B cells whereas CR is a complement receptor present on B cells but not T cells.

Studies of these synthetic peptides in the induction assay in vitro showed them to have the same induction sepcificity as Thymopoietin II. That is, they induced the differentiation of Thy-1− cells to Thy-1+ T cells, but did not induce the differentiation of CR− cells to CR+ cells. While many substances have been identified that can mimic Thymopoietin in vitro and induce T cell differentiation by raising intracellular cyclic AMP, it is emphasized that few substances are active at such low concentration and the peptides of this invention are selective in inducing T cell differentiation but not CR+ B cell differentiation. These synthetic peptides were also shown to affect neuromuscular transmission, like Thymopoietin itself. Thus, 24 hours after a single injection of 10–100 $\mu$g per mouse, there was a definite neuromuscular transmission impairment detectable by electromyography.

Because of these characteristics of the polypeptides of this invention, they are therapeutically useful in the treatment of humans and animals since they have the capability for inducing the differentiation of lymphopoietic stem cells originating in the haemopoietic tissues to thymus derived cells or T cells which are capable of involvement in the immune response to the body. As a result, the products of this invention are considered to have multiple therapeutic uses. Primarily, since the compounds have the capability of carrying out certain of the indicated functions of the thymus, they have application in various thymic function and immunity areas. A primary field of application is in the treatment of DiGeorge Syndrome, a condition in which there is a congenital absence of thymus. Injection of the polypeptides will overcome this deficiency. Because of their biological characteristics, which are extremely active at low concentrations, they are considered useful in assisting the collective immunity of the body in that the polypeptides will increase or assist in therapeutic stimulation of cellular immunity and thereby become useful in the treatment of diseases involving chronic infection in vivo, such as fungal or mycoplasma infections, tuberculosis, leprosy, acute and chronic viral infections, and the like. Further, the compounds are considered to be useful in any area in which cellular immunity is an issue and particularly where there are deficiencies in immunity such as in the DiGeorge Syndrome mentioned above. Also, where there is an excess of antibody production due to unbalanced T cells and B cells, the compounds can correct this condition by stimulating T cell production. Thus, they may be of therapeutic use in certain autoimmune diseases in which damaging antibodies are present, for example, systemic lupus erythematosus. Further, because of the characteristics of the polypeptides they have in vitro usefulness in inducing the development of surface antigens of T cells, in inducing the development of the functional capacity to achieve responsiveness to mitogens and antigens and cell collaborativity in enhancing the ability of B cells to produce antibodies. The polypeptides are also useful in inhibiting the uncontrolled proliferation of Thymopoietin-responsive lymphocytes.

An important characteristic of the polypeptides is their in vivo ability to restore cells with the characteristic of the T cells. Therefore, the polypeptides of this invention are active in many areas as a result of their ability to enhance the immune response in the body. Since the polypeptides of this invention affect neuromuscular transmission, very high doses of the peptides of this invention will be useful in treating diseases with excess neuromuscular transmission, such as spasticity.

A further important property of the peptides of this invention is that they are highly active in very low concentrations ranging from 1 nanogram per ml, and are maximally active at concentrations from about 100 nanogram per ml. The carrier may be any of the well known carriers for this purpose including normal saline solutions, preferably with a protein diluent such as bovine serum albumin to prevent adsorptive losses to glassware at these low concentrations. The peptides of this invention are active at a range of above about 1 mg/kg of body weight. For the treatment of DiGeorge Syndrome, the polypeptides may be administered at a rate of about 1.0 to 10 mg/kg of body weight. Generally, the same range of dosage amounts may be used in treatment of the other conditions or diseases mentioned.

The basic pentapeptides of this invention were prepared using concepts similar to the method of Merrifield as reported in *Journal of American Chemical Society*, 85, pp. 2149-2154, 1963. The synthesis involved the stepwise addition of protected amino acids to a growing peptide chain which was bound by covalent bonds to a solid resin particle. By this procedure, reagents and by-products were removed by filtration and the recrystallization of intermediates as eliminated. The general concept of this method depends on attachment of the first amino acid of the chain to a solid polymer by a covalent bond and the addition of the succeeding amino acids one at a time in a stepwise manner until the desired sequence is assembled. Finally, the peptide is removed from the solid support and protecting groups removed. This method provides a growing peptide chain attached to a completely insoluble solid particle so that it is in a convenient form to be filtered and washed free of reagents and by-products.

The amino acids may be attached to any suitable polymer which merely has to be insoluble in the solvents used and have a stable physical form permitting ready filtration. It must contain a functional group to which the first protected amino acid can be firmly linked by a covalent bond. Various polymers are suitable for this purpose such as cellulose, polyvinyl alcohol, polymethylmethacrylate and sulfonated polystyrene but in the synthesis of this invention, there was used a chloromethylated copolymer of styrene and divinylbenzene.

The various functional groups on the amino acid which were active but which were not to enter into the reactions were protected by conventional protecting groups as used in the polypeptide art throughout the reaction. Thus, the functional groups such as the side chain on arginine, lysine, aspartic acid, and tyrosine were protected by protecting groups which could be removed on completion of the sequence without adversely affecting the polypeptide final product. The synthesis was performed by a modification of the solid synthesis method in that fluorescamine was used to determine if coupling was complete by an indication of positive fluorescence (see Felix, et al., *Analyt. Biochem.*, 52, 377, 1973). If complete coupling was not indicated, the coupling was repeated with the same protected amino acid before α-amino deprotection.

The general procedure involved initially esterifying L-tyrosine, protected on its amino and hydroxyl groups, to the resin in absolute alcohol containing an amine. The coupled amino acid resin was then filtered, washed with alcohol and water and dried. The protecting group on the amino group of the protected tyrosine (e.g., t-benzyloxycarbonyl, abbreviated as t-BOC), was then removed without affecting other protecting groups. The resulting coupled amino acid-resin, having the free amino group, was then reacted with a protected L-valine, preferable alpha t-BOC-L-valine to couple the L-valine to the amino acid-resin. The reactions were then repeated with protected L-aspartic acid, L-lysine and L-arginine until the complete molecule was prepared. This procedure was used in formation of the basic five-amino acid active sequence. The addition of other neutral amino acid residues on either end of the chain is carried out using the same sequence of reactions as known in the art. The sequence of reactions to prepare the five member amino acid active site may be carried out as follows:

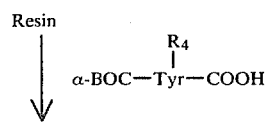

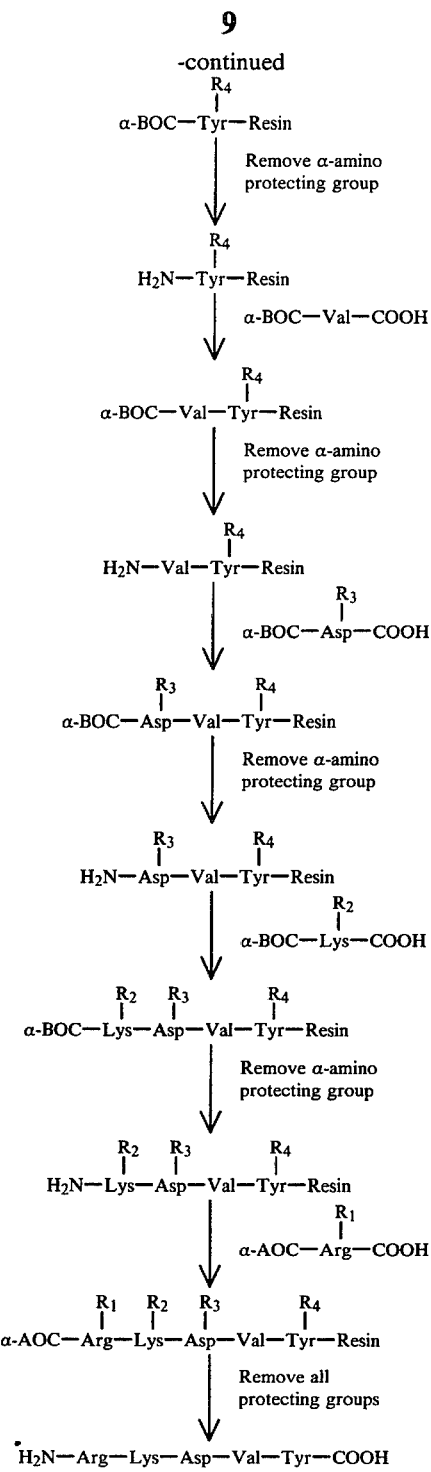

In the above sequence of reactions $R_1$, $R_2$, $R_3$, and $R_4$ are protecting groups on the various reactive groups on the amino acid side chains which are not affected or removed when the α-amino protecting group is removed to permit further reaction. Preferably, in the above intermediate pentapeptide resin, the expression $R_1$ is tosyl (Tos), $R_2$ stands for benzyloxycarbonyl (Z), $R_3$ stands for benzyl (Bzl), $R_4$ stands for 0-2,6-dichlorobenzyl, and α-$R_5$ is t-amyloxycarbonyl (tAOC). The resin is any of the resins mentioned above as being useful in the process.

The peptide-resin is cleaved to free the peptide from the resin and protecting groups $R_1$, $R_2$, $R_3$, $R_4$, and α-$R_5$ simultaneously to provide the final product polypeptide. The protecting groups and resin were cleaved by conventional means, e.g., by treatment with anhydrous fluoride and the peptide recovered.

While the preferred method for production of the polypeptides of this invention is by the use of an insoluble solid polymer as described in the method of Merrifield, it is also to be understood that other methods for preparations may also be used. For example, a different solid support may be employed such as an N-methyl-benzhydrylamine resin or benzhydrylamine resin, which is advantageous under certain conditions. In this procedure the C-terminal amino acid is attached directly to the resin and the finished peptide may be cleaved from the substrate in HF to form C-terminal amides. Techniques for use of an N-methyl-benzhydrylamine resin are described by Monahan, et al., in *Biochemical and Biophysical Research Communications*, 48, 1100–1105 (1972). Techniques for use of a benzhydrylamine resin are described by J. Rivier, et al., in *Journal of Medicinal Chemistry*, 1973, vol 16, p 545–549.

Various derivatives of the basic pentapeptide may also be produced using methods known to the art. Obviously, in the production of such derivatives it will be necessary to block functional groups which might interfere with the reaction sequence in order to produce the desired product. For example, the alpha-carboxylic acid group of aspartic acid or the alpha-amino group of lysine should be blocked during preparation of these derivatives.

As pointed out above, in conducting the process it is necessary to protect or block the amine groups in order to control the reaction and obtain the products desired. Suitable amino-protecting groups which may be usefully employed include salt formation for protecting strongly-basic amino groups, or urethane protecting substituents such as benzyloxycarbonyl and t-butyloxycarbonyl. It is preferred to utilize tert-butyloxycarbonyl (tBOC) or t-amyloxycarbonyl (tAOC) for protecting the α-amino group in the amino acids undergoing reaction at the carboxyl end of the molecule, since the BOC and AOC protecting groups are readily removed following such reaction, and prior to the subsequent step (wherein such α-amino group itself undergoes reaction), by relatively mild action of acids (e.g., trifluoroacetic acid). This treatment does not otherwise affect protecting groups on said chains. It will thus be understood that the α-amino group may be protected by reaction with any material which will protect the α-amino group for the subsequent reaction(s) but which may later by removed under conditions which will not otherwise affect the molecule. Illustrative of such materials are organic carboxylic acid derivatives which will acylate the amino group.

In general, the amino groups can be protected by reaction with a compound containing a grouping of the formula:

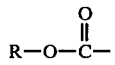

wherein R is any grouping which will prevent the amino group from entering into subsequent coupling reactions and which can be removed without destruction of the molecule. Thus, R is a straight or branched chain alkyl which may be unsaturated, preferably of 1 to 10 carbon atoms; aryl, preferably of 6 to 15 carbons;

cycloalkyl, preferably of 5 to 8 carbon atoms; aralkyl, preferably of 7 to 18 carbon atoms; alkaryl, preferably of 7 to 18 carbon atoms; or heterocyclic, e.g. isonicotinyl. The aryl, aralkyl, and alkaryl moieties may also be further substituted as by one or more alkyl groups of 1 to about 4 carbon atoms. Preferred groupings for R include tertiary-butyl, tertiary-amyl, phenyl, tolyl, xylyl, and benzyl. Highly preferred specific amino-protecting groups include benzyloxycarbonyl; substituted benzyloxycarbonyl wherein the phenyl ring is substituted by one or more halogens, e.g., Cl or Br; nitro; lower alkoxy, e.g., methoxy; lower alkyl; tertiary-butyloxycarbonyl; tertiary-amyloxycarbonyl; cyclohexyloxycarbonyl; vinyloxycarbonyl; adamantyloxycarbonyl; biphenylisopropoxycarbonyl; and the like. Other protecting groups which can be used include isonicotinyloxycarbonyl, phthaloyl, para-tolysulfonyl, formyl and the like.

In conducting the general process of the invention, the peptide is built by reaction of the free α-amino group with a compound containing a blocked α-amino group. For reaction or coupling, the carboxyl component of the compound being attacked is activated at its carboxyl group so that the carboxyl group can then react with the free α-amino group on the peptide chain. To achieve activation, the carboxyl group can be converted to any reactive group such as an ester, anhydride, azide, acid chloride, or the like. It should also be understood that during these reactions, the amino acid moieties contain both amino groups and carboxyl groups and usually one grouping enters into the reaction while the other is protected. Prior to the coupling step, the protecting group on the alpha- or terminal-amino group of the peptide attached to the resin is removed under conditions which will not substantially affect other protecting groups, e.g., the groups on the epsilon-amino group of the lysine molecule. The preferred procedure for effecting this step is mild acid hydrolysis, as by reaction at room temperature with trifluoroacetic acid.

As may be appreciated, the above-described series of process steps results in the production of the specific pentapeptide of the following formula:

This pentapeptide also includes the basic active-site sequence of the polypeptide of this invention. The substituted pentapeptide of Formula II, wherein the terminal ARG and TYR amino acid groups may be further substituted as described above, are then prepared by reaction of this basic pentapeptide with suitable reagents to prepare the desired derivatives. Reactions of this type such as acylation, esterification, amidation and the like, are of course well known in the art. Further, other amino acids, that is amino acid groups which do not affect the biological activity of the basic pentapeptide molecule, may be added to the peptide chain by the same sequence of reactions by which the pentapeptide was synthesized.

The following examples are presented to illustrate the invention but it is not to be considered as limited thereto. In the Examples and throughout the specification, parts are by weight unless otherwise indicated.

EXAMPLE I

In preparation of the polypeptide of this invention the following materials were purchased commercially.

Alpha-AOC-Ng-Tos-L-arginine
Alpha-BOC-2-chloro-benzyloxycarbonyl-L-lysine
Alpha-BOC-O-benzyl-L-aspartic acid
Alpha-BOC-L-valine
Alpha-BOC-2,6-dichlorobenzyl-L-tyrosine In these reagents, BOC is t-butyloxycarbonyl, AOC is t-amyloxycarbonyl, and Tos is tosyl. "Sequenal" grade reagents for amino acid sequence determination, dicyclohexyl carbodiimide, flurescamine, and the resin were also purchased commercially. The resin used was a polystyrene divinyl benzene resin, 200–400 mesh size containing 1% divinyl benzene and 0.75 mM of chloride per gram of resin.

In preparation of the polypeptide, 2 m moles of α-BOC-O-2,6-dichlorobenzyl-L-tyrosine were esterified to 2 m moles chloromethylated resin in absolute alcohol containing 1 mM triethylamine for 24 hours at 80° C. The resulting coupled amino acid resin was filtered, washed with absolute alcohol, and dried. Thereafter, the α-BOC or α-AOC amino acids were similarly coupled to the deprotected α-amino group of the peptide-resin in the correct sequence to result in the polypeptide of this invention using equivalent amounts of dicyclohexyl carbodiimide. After each coupling reaction, an aliquot of resin was tested with fluorescamine and if positive fluorescence was found, coupling was taken to be incomplete and was repeated with the same protected amino acid. As the result of the several coupling reactions, the following pentapeptide-resin resulted:

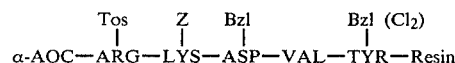

where AOC is amyloxycarbonyl, Tos is tosyl, Z is benzyloxycarbonyl, and Bzl is benzyl, and Bzl (Cl₂) is O-2,6-dichlorobenzyl.

This peptide-resin was cleaved and the protecting groups removed in a Kelf cleavage apparatus (Peninsula Laboratories, Inc.) using anhydrous hydrogen fluoride at 0° C. for 60 minutes with 1.2 ml anisole per gram peptide-resin as scavenger. The peptide mixture was lyophilized and washed with anhydrous ether and the peptide extracted with glacial acetic acid and water. The peptide was chromatographed on P-6 Bio-Gel in 1 N acetic acid. The resulting polypeptide was determined to be 94% pure and was determined to have the following sequence:

EXAMPLE II

To determine the activity and characteristics of the polypeptide, determinations were carried out on healthy 5–6 week nu/nu mice of both sexes, the mice being bred on a BALB/c background (thymocytes expressing Thy-1.2 surface antigen) and maintained under conventional conditions. For the antisera, anti Thy-1.2 sera were prepared in Thy-1 congenic mice.

For the induction in vitro of Thy-1+ T cells or CR+ B cell differentiation, the induction of thymocyte differentiation from prothymocytes in vitro was performed as described by Komuro and Boyse, (Lancet, 1, 740, 1973), using the acquisition of Thy-1.2 as a marker of T cell differentiation. The induction of CR+ B cell differentiation from CR− B cell precursors in vitro was performed under similar conditions using as the assay criterion, the capacity of CR+ B cells to bind sheep erythrocytes coated with sub-agglutinating quantities of rabbit antibody and nonlytic complement. Spleen cell populations from healthy nu/nu mice fractionated on discontinuous bovine serum albumin gradients were used as the source of both precursor types (Thy-1⁻ and CR⁻) because they have few or no Thy-1+ cells and low numbers of CR+ cells.

As a result of this determination it was found that the polypeptide displayed a selectivity of actions similar to that of Thymopoietin II in inducing the differentiation of T-lymphocytes but not of complement receptors (CR+) B-lymphocytes. The pentapeptide induced differentiation of Thy-1+ T cells in concentrations ranging from 1 ng to 10 μg/ml. It did not induce the differentiation of CR+ B cells in concentrations of 0.01 ng to 10 μg/ml.

EXAMPLE III

To determine the effect of this peptide on neuromuscular transmission, mice were injected with 10–100 μg peptide in N saline intraperitoreally. Twenty-four hours later, neuromuscular transmission was assessed by electromyography as described in *Lancet*, Vol. 12, pp. 256–259, 1975. There was a detectable neuromuscular impairment in the mice injected with the peptide.

EXAMPLE IV

The pentapeptide of Example I is prepared on a substrate comprising a benzhydrylamine resin using the method of J. Rivier, et al., *Journ. Med. Chem.*, Vol. 16, No. 5, pp. 545-8 (1973). In the synthesis, dicyclohexylcarbodiimide is the coupling agent and the coupling is carried out in $CH_2Cl_2$. The peptide is then cleaved from the substrate with hydrogen fluoride to free the peptide and remove protective groups and form the following derivative:

$$H_2N—ARG—LYS—ASP—VAL—TYR—CONH_2$$

For identification, thin layer chromatography and electrophoresis were employed which provided the following data:

| Thin Layer Chromatography | | | | |
|---|---|---|---|---|
| Sample: 30 μg | | | | |
| Silica gel (Brinkman glass plate 5 × 20 cm, 0.25mm thickness) | | | | |
| $R_f^1$ : n-BuOH | :Pyridine | :HOAc:$H_2O$ | 30:15:3:12 | |
| $R_f^2$ : EtOAc | :Pyridine | :HOAc:$H_2O$ | 5:5:1:3 | |
| $R_f^3$ : EtOAc | :n-BuOH | :HOAc:$H_2O$ | 1:1:1:1 | |
| Spray reagent: Pauly, Ninhydrin, and $I_2$. | | | | |

| | TLC | | | Electrophoresis Peptide moved to |
|---|---|---|---|---|
| Compounds | $R_f^1$ | $R_f^2$ | $R_f^3$ | cathode |
| Arg—Lys—Asp—Val—Tyr—$NH_2$ | 0.53 | 0.68 | 0.26 | 7.5cm |
| Electrophoresis: | | | | |
| Whatman 3mm paper (11.5cm × 56cm) | | | | |
| Sample: 100 μg | | | | |
| pH 5.6, Pyridine acetate buffer solution | | | | |
| 1000 V, 1 hour | | | | |
| Spray reagent: Ninhydrin and Sakaguchi | | | | |

This amidated pentapeptide, when utilized in a concentration of 1 μg/ml in 89% Twomey solution, showed a maximum activity of 105%, and a minimum activity of 70%, when compared with the basic pentapeptide of Example I.

EXAMPLE V

The basic pentapeptide prepared in Example I is esterified to produce the ethyl alcohol derivative. In preparation of this ester it is necessary to block the acid group on aspartic acid with a mild acid sensitive blocking group during preparation, with the preferred blocking group being t-butyl. The α-amino blocking group is sensitive to mild base, and is preferably fluorenylmethoxy carbonyl. When using such an α-amino blocking group, it may be removed for the addition of each amino acid residue without disturbing the acid-sensitive protecting group on the aspartic acid residue. After preparation of the protected pentapeptide resin, treatment with mild base followed by treatment with mild acid will remove these two protecting groups. Transesterification with ethyl formate using sulfuryl chloride as a catalyst will cleave the pentapeptide from the resin to selectively form the C-terminal ester. Esterification will not occur at the free acid group of the aspartic acid residue. The remaining protective groups are removed and the peptide of the following formula is recovered:

$$H_2N—ARG—LYS—ASP—VAL—TYR—COOC_2H_5$$

EXAMPLE VI

In this example the pentapeptide of Example I is prepared using an N-methyl-benzhydrylamine resin as the solid support following the method of Monahan, et al., *Biochemical and Biophysical Research Communications*, vol. 48, 1100–1105 (1972). The protected pentapeptides is then cleaved from the resin with hydrogen fluoride to prepare the following amide substituted derivative:

$$H_2N—ARG—LYS—ASP—VAL—TYR—CONHCH_3$$

EXAMPLE VII

In this example the N-methyl-substituted derivative of the basic pentapeptide of Example I is prepared following the procedure of Example I but substituting for the protected L-arginine used therein an equivalent amount of protected N-methyl-L-arginine. The peptide of the following formula is produced:

$$CH_3NH—ARG—LYS—ASP—VAL—TYR—COOH$$

EXAMPLE VIII

The methyl amino polypeptide prepared as in Example VII is prepared using the benzylhydrylamine resin as the solid support as described in Example IV. The resulting protected and supported pentapeptide is then cleaved from the resin with hydrogen fluoride, protective groups are removed, and there is formed the amido polypeptide of the following formula:

$$CH_3NH—ARG—LYS—ASP—VAL—TYR—CONH_2$$

EXAMPLE IX

Following the procedure of Example V, but substituting for the protected L-arginine used therein an equivalent amount of protected N-methyl-L-arginine, the following esterified polypeptide is prepared.

CH₃NH—ARG—LYS—AS-
P—VAL—TYR—COOC₂H₅

EXAMPLES X to XX

Using the reaction techniques described hereinabove for the lengthening of the polypeptide chain, the following polypeptides are prepared which contain the active amino acid sequence but which are substituted on the terminal amino and carboxylic groups by R and R' to provide the basic amino acid of the formula:

R—HN—ARG—LYS—ASP—VAL—TYR—COR' which is substituted by the amino acids given in the following Table as indicated.

| EXAMPLE NO. | R | R' |
|---|---|---|
| X | GLN | OH |
| XI | GLU—GLN | OH |
| XII | GLY—GLU—GLN | OH |
| XIII | GLY—GLU—GLN | VAL |
| XIV | GLY—GLU—GLN | VAL—GLN |
| XV | GLY—GLU—GLN | VAL—GLN—LEU |
| XVIq | GLY—GLU—GLN | VAL—GLN—LEU—TYR |
| XVII | GLN | VAL |
| XVIII | GLN | VAL—GLN |
| XIX | GLN | VAL—GLN—LEU |

EXAMPLE XX

The protected pentapeptide prepared as in Example I, while still coupled to the resin, is treated with trifluoroacetic acid in dichloromethane to remove the t-AOC protecting group from the arginine moiety. The resulting peptide is then acylated with acetic anhydride, followed by cleavage from the resin substrate and removal of all protecting groups with HF. The following acylated derivative is thus produced:

CH₃CONH—ARG—LYS—AS-
P—VAL—TYR—COOH

The polypeptide derivatives prepared in Examples V-XX retain the biological activity as described herein for the basic amino acid sequence.

The invention has been described herein with reference to certain preferred embodiments. However, as obvious variations will appear to those skilled in the art, the invention is not to be considered as limited thereto.

What is claimed is:

1. An intermediate polypeptide of the following sequence:

$$\begin{array}{cccc} R_1 & R_2 & R_3 & R_4 \\ | & | & | & | \\ R_5-ARG-LYS-ASP-VAL-TYR-\text{Resin} \end{array}$$

wherein $R_1$, $R_2$, $R_3$, $R_4$ and $R_5$ are protecting groups with $R_1$, $R_2$, $R_3$ and $R_4$ being protecting groups on reactive side chains, and wherein the $R_5$ protecting group is on an amino group of the ARG amino acid and is removable under conditions which do not affect the $R_1$, $R_2$, $R_3$ and $R_4$ groups, and the resin is an insoluble polymer having a stable physical form and is attached to a carboxyl group of the TYR amino acid through a functional group of the resin by a covalent bond.

2. An intermediate polypeptide according to claim 1 wherein $R_1$ is tosyl, $R_2$ is ε-2-chlorobenzyloxycarbonyl, $R_3$ is benzyl, $R_4$ is O-2,6-dichlorobenzyl, and $R_5$ is amyloxy carbonyl.

* * * * *